United States Patent
Dunn et al.

(10) Patent No.: US 12,312,162 B2
(45) Date of Patent: May 27, 2025

(54) FLEXIBLE BAG ASSEMBLY

(71) Applicant: MUNCHKIN, INC., Van Nuys, CA (US)

(72) Inventors: Steven Bryan Dunn, Beverly Hills, CA (US); Kevin Douglas Johnson, Tarzana, CA (US)

(73) Assignee: MUNCHKIN, INC., Van Nuys, CA (US)

( * ) Notice: Subject to any disclaimer, the term of this patent is extended or adjusted under 35 U.S.C. 154(b) by 395 days.

(21) Appl. No.: 17/736,989

(22) Filed: May 4, 2022

(65) Prior Publication Data

US 2022/0356009 A1 Nov. 10, 2022

Related U.S. Application Data

(60) Provisional application No. 63/184,173, filed on May 4, 2021.

(51) Int. Cl.
| | |
|---|---|
| *B65F 1/00* | (2006.01) |
| *A61L 2/10* | (2006.01) |
| *A61L 2/26* | (2006.01) |
| *A61L 11/00* | (2006.01) |
| *B65F 1/06* | (2006.01) |

(Continued)

(52) U.S. Cl.
CPC .............. *B65F 1/0006* (2013.01); *A61L 2/10* (2013.01); *A61L 2/26* (2013.01); *A61L 11/00* (2013.01); *B65F 1/06* (2013.01); *B65F 1/16* (2013.01); *B65F 7/00* (2013.01); *A61L 2202/11* (2013.01); *A61L 2202/121* (2013.01); *A61L 2202/122* (2013.01); *B65F 2240/132* (2013.01); *B65F 2250/105* (2013.01)

(58) Field of Classification Search
CPC .. B65F 1/0006; B65F 1/06; B65F 1/16; B65F 7/00; B65F 2240/132; B65F 2250/105; B65F 1/062; B65F 1/12; A61L 2/10; A61L 2/26; A61L 11/00; A61L 2202/11; A61L 2202/121; A61L 2202/122; A61L 2202/181

See application file for complete search history.

(56) References Cited

U.S. PATENT DOCUMENTS

| | | | | |
|---|---|---|---|---|
| 5,444,113 | A  * | 8/1995 | Sinclair  .................. | D21H 17/53 523/124 |
| 9,714,138 | B2 * | 7/2017 | Dunn ........................ | B65F 1/06 |

(Continued)

FOREIGN PATENT DOCUMENTS

WO 2013134124 A1 9/2013

OTHER PUBLICATIONS

International Preliminary Report On Patentability and Written Opinion for PCT/US2022/27727, mailed Jul. 20, 2022. (p. 12).

*Primary Examiner* — David A Vanore
(74) *Attorney, Agent, or Firm* — Robert Z. Evora, Esq.

(57) ABSTRACT

A flexible bag assembly having at least one layer of a flexible material that permits a UV light source to penetrate through to sterilize bacterial contents on an interior of the flexible bag assembly. Transmission of the UV light source is maximized through the flexible material and to enhance a kill rate of bacteria within the interior of the flexible bag assembly. A bio-assimilator may be integrated into a composition of the flexible bag assembly to facilitate biodegradation by anaerobic degradation leaving no microplastic remnants.

20 Claims, 18 Drawing Sheets

(51) Int. Cl.
    *B65F 1/16*     (2006.01)
    *B65F 7/00*     (2006.01)

(56) References Cited

U.S. PATENT DOCUMENTS

| | | | |
|---|---|---|---|
| 10,906,737 B2 * | 2/2021 | Dunn | B65F 1/062 |
| 11,167,918 B2 * | 11/2021 | Dunn | B65F 1/0073 |
| 11,565,012 B2 * | 1/2023 | Grenon | A61L 2/26 |
| 11,794,992 B2 * | 10/2023 | Wang | A61L 9/14 |
| 2010/0005759 A1 * | 1/2010 | Stravitz | B65F 1/062 53/118 |
| 2010/0005762 A1 * | 1/2010 | Stravitz | B65F 1/062 53/567 |
| 2011/0099950 A1 * | 5/2011 | Dunn | B65F 1/062 53/469 |
| 2011/0099956 A1 * | 5/2011 | Dunn | B65F 7/00 383/127 |
| 2011/0099957 A1 * | 5/2011 | Dunn | B65F 1/06 53/567 |
| 2011/0099958 A1 * | 5/2011 | Dunn | B65F 1/0006 53/567 |
| 2014/0042168 A1 * | 2/2014 | Dunn | B65F 1/0006 220/495.05 |
| 2018/0110893 A1 * | 4/2018 | Chang | A61L 9/20 |
| 2020/0158601 A1 * | 5/2020 | Scally | C08J 5/18 |
| 2021/0085819 A1 * | 3/2021 | Brewster | A61L 15/60 |
| 2021/0283286 A1 * | 9/2021 | Dunn | B65F 1/163 |
| 2021/0283288 A1 * | 9/2021 | Dunn | B65F 1/062 |
| 2021/0290798 A1 * | 9/2021 | Johnson | B65F 1/163 |
| 2021/0379425 A1 * | 12/2021 | Tran | A62B 23/06 |
| 2022/0356009 A1 * | 11/2022 | Dunn | A61L 2/26 |

* cited by examiner

FLEXIBLE BAG ASSEMBLY

CROSS REFERENCE TO RELATED APPLICATION

This Non-Provisional U.S. application claims priority to U.S. Provisional Patent Application Ser. No. 63/184,173 filed May 4, 2021, the content of which is hereby incorporated by reference herein in its entirety into this disclosure.

TECHNICAL FIELD

The subject disclosure relates generally to a flexible bag assembly for use in a waste container or diaper pail. The flexible bag assembly may be a single use flexible bag or a cassette for dispensing tubing and may be biodegradable and/or optimized for ultraviolet light sterilization generated by a UV sterilizing pail.

BRIEF DESCRIPTION OF THE DRAWINGS

Various exemplary embodiments of this disclosure will be described in detail, wherein like reference numerals refer to identical or similar components or steps, with reference to the following figures, wherein.

DETAILED DESCRIPTION

Particular embodiments of a flexible bag assembly 100 will now be described in greater detail with reference to the figures.

Figure 1:
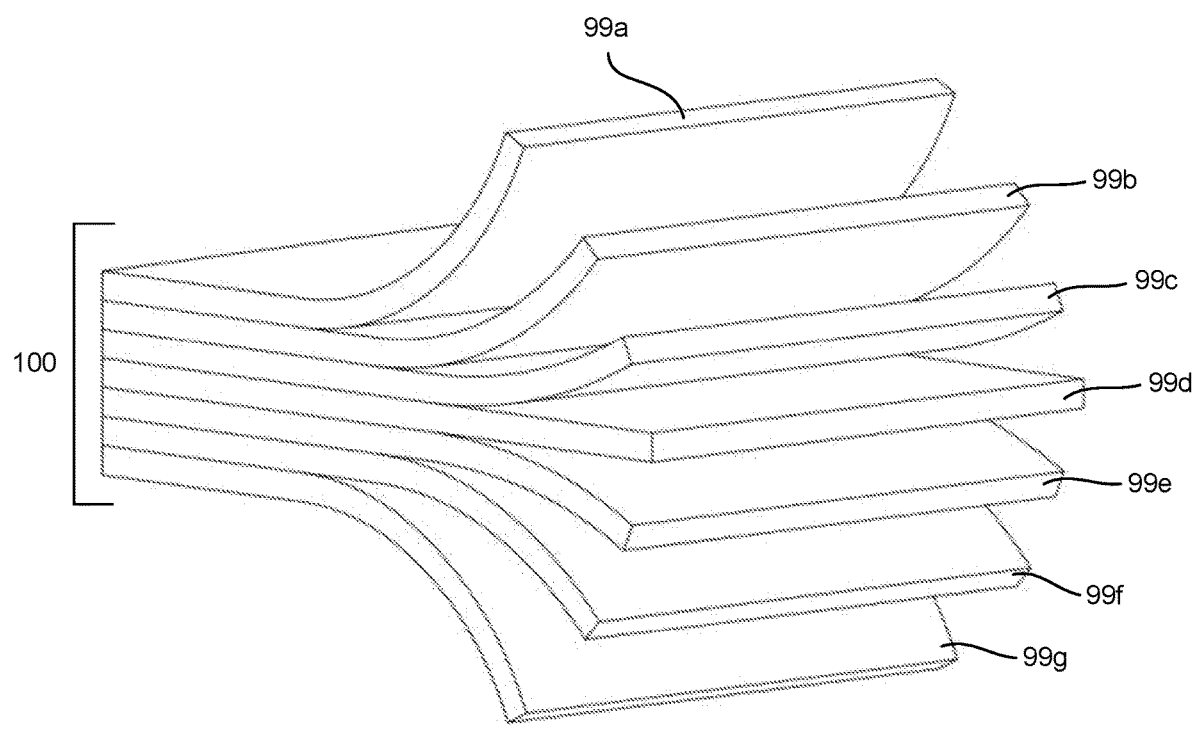
FIG. 1 is a is a close-up view of the layers of a flexible bag assembly, according to an exemplary embodiment of the present subject disclosure.

FIG. 1 shows the layered composition of an exemplary flexible bag assembly 100 according to this subject disclosure. The flexible bag assemblies 100 may include multiple layers of flexible material in their construction. One exemplary embodiment of a flexible bag assembly 100 is a single use flexible bag 110 having seven layers. Another exemplary embodiment of the flexible bag assembly 100 is a cassette 101 having flexible tubing 106 that has a seven-layer composition. A first layer 99a may be comprised of polyethylene (PE) and/or low-density polyethylene (LDPE), and may include a slip agent or antiblock compound. A second layer 99b may be comprised of PE, LDPE, and/or linear low-density polyethylene (LLDPE). The second layer 99b may include a pigment, slip agent or antiblock compound. A third layer 99c may be comprised of an anhydride-modified, LLDPE resin. A fourth layer 99d may be comprised of an ethylene vinyl alcohol (EVOH) copolymer. A fifth layer 99e may be comprised of an anhydride modified, LLDPE resin. A sixth layer 99f may be comprised of PE, LDPE and/or LLDPE and may include a pigment, slip agent or antiblock compound. A seventh layer 99g may be comprised of PE, LDPE, and may include a slip agent or antiblock compound.

Additionally, the flexible bag assemblies 100 may be comprised completely or partially of one or more biopolymers, such as starch, cellulose derivatives, natural rubbers, polyimides, bio-monomers (polyimides, polyurethanes, polybutylene succinate (PBS), Polyhydroxyalkanoates (PHAs), Poly(3-hydroxybutyrate-co-3hydroxyvalerate) (PHBV), bio-based PE, bio-based polyethylene terephthalate (Bio-PET), polylactic acid (PLA), and the like according to this subject disclosure. Biodegradable Plastics maintain their mechanical strength during practical use but break down into low-weight compounds and non-toxic byproducts at the end of their lifecycle. Such materials can be obtained through chemical synthesis, fermentation by microorganisms, and from chemically modified natural products.

Fluorinated Ethylene Propylene (FEP) is one material that exhibits excellent transmission of UV light. FEP is used for components in the Hubble Space Telescope and the International Space Station because of its robust material properties that are able to withstand the harsh demands of outer space. FEP tubing may transmit UV light effectively without suffering the degradation caused by photo-oxidation and unwanted polymer cross-linking associated with the effects of UV light on other consumer plastic products. FEP may be the primary component in any layer 99a-g of the flexible bag assemblies 100.

The layers 99a-g of the flexible bag assemblies 100 may be of interchangeable and may be layered in any order. The flexible bag assemblies 100 may have different layer configurations, or number of layers, using the above listed materials, or similar. For example, the flexible bag assembly 100 may be formed of eleven layers, nine layers, five layers (99b-f), three layers (99b-d), or a single layer, and the like according to this subject disclosure.

The flexible bag assemblies 100 may be adapted to effectively transmit UV light, such that the inner surface of the bag 100 and contents of the flexible bag assemblies 100 will also be sterilized. The ability of UV light, especially UV-C light to penetrate materials is dependent, in large part, on the chemical and structural composition of the materials. In order to create flexible bag assemblies 100 capable of effectively transmitting UV light, it is necessary to balance the chemical contents of the materials used therein. Stabilizer, blockers, absorbers, antioxidants, pigments and other additives may be used in the flexible bag assemblies 100 such that they do not interfere with the transmission of UV light. In one embodiment, all layers 99a-g of the flexible bag assembly 100 may be clear (without pigment) in order to promote the transmission of UV light into the flexible bag assembly 100.

An advantage of the subject disclosure is the ability to effectively transmit UV light through the flexible bag assemblies 100, such that the inner surfaces of the bag, as well as into the contents within the flexible bag assemblies 100 will also be sterilized in an efficient manner. That is, the reduction rate of the transmission of the UV light through the bag film is minimal and/or significantly less employing the material composition of the bag film of the instant subject disclosure than with other commercially available diaper bags. This advantage results in an enhanced kill rate of bacterial within the interior of the flexible bag assemblies 100 from the interior wall deep into the bag film itself.

Another of the advantages to a multi-layer bag relative to the transmission of UV light is the relative thinness of the individual layers 99a-g that the UV light must pass through. The layers 99a-g of the flexible tubing 106 of the cassette may be substantially between 9-30 microns in order to minimize the overall gauge width of the flexible tubing 106 that UV light must pass through in order to reach the inside of the bag 100. In one embodiment, a PE layer of the flexible tubing 106 of the cassette may have a width of 21 microns. Additionally, the layers 99a-g of the single use flexible bag 110 may be substantially between 14-45 microns in order to minimize the overall gauge width of the single use flexible bag 110 that UV light must pass through in order to reach the inside of the bag 100. In one embodiment, a PE layer of the single use flexible bag 110 may have a width of 30 microns.

The layers 99a-g of the flexible bag assemblies 100 may include a bio-assimilator compound, such as ECLIPSE™. Traditional plastic materials like PE may be difficult to degrade in the environment. A bio-assimilator is a compound that degrades plastic to a molecular weight that can be consumed by living organisms. This is a final and conclusive stage of plastic biodegradation that leaves behind no microplastic remnants. The addition of a bio-assimilator to polyolefins like PE can be tailored to ensure a useful-life performance before degrading according to a set time-table. For example, a bio-assimilator may be added to any of the layers 99a-g with a simple inclusion rate between 0.01-2% concentration (w/w=mass of solute/mass of solution×100) in the masterbatch or at any time during the finished film production process. Additionally, a bio-assimilator may comprise between 0.01-10% concentration of the plastic formulation used to manufacture the flexible bag assemblies 100. In one embodiment, the flexible bag assembly 100 may be manufactured to contain approximately 1% of the final weight of the flexible bag assembly. The flexible bag assembly 100 may be adapted to degrade between 1 and 60 months. In one embodiment the flexible bag assembly 100 may be adapted to degrade between 18-24 months. In another embodiment the flexible bag assembly may be adapted to degrade in approximately 36 months.

Bio-assimilation may be seen as a later stage of the more general process of biodegradation. Biodegradation is the process by which organic or related artificial substances are broken down through the enzymatic or metabolic processes of living microbial organisms. This process can be divided into three stages: bio-deterioration, bio-fragmentation and assimilation. Bio-deterioration modifies the mechanical, physical and chemical properties of the material and can occur when the substance is exposed to abiotic factors in the environment. Bio-fragmentation of a polymer is the lytic process in which bonds are cleaved, thereby generating oligomers and monomers as a result. In the assimilation stage, the resulting products from bio-fragmentation are integrated into microbial cells. Biodegradation can occur aerobically, with oxygen, or anaerobically, without oxygen.

Aerobic biodegradation is the breakdown of a substance by microorganisms when oxygen is present and, therefore, the chemistry of the relevant system, environment, or organism is characterized by oxidative conditions. Aerobic bacteria (aerobes) have an oxygen-based metabolism, and in a process called cellular respiration, use oxygen to oxidize substrates to obtain energy. Many organic substances are rapidly degraded under aerobic conditions by aerobes.

Anaerobic biodegradation occurs when the system or environment lacks oxygen or anaerobic microbes are dominant over aerobic microbes. Biodegradable waste in landfills degrade in the absence of oxygen through the process of anaerobic digestion. Anaerobic digestion is widely used to treat wastewater sludge and other biodegradable waste because it provides volume and mass reduction of the input material. In an integrated waste management system, anaerobic digestion reduces the emission of landfill gas (biogas) into the atmosphere. Biogas contains methane which has approximately 21 times the global warming potential as carbon dioxide. The methane and carbon dioxide rich biogas generated by anaerobic biodegradation is an excellent renewable energy source. The nutrient-rich solids (humus) left over after digestion can also be used as fertilizer.

Oxo-biodegradation is defined by CEN as "degradation resulting from oxidative and cell-mediated phenomena, either simultaneously or successively." It is distinguished from the term "oxo-degradable," which only refers to the first oxidative phase of degradation and does not include the later bio-assimilation applied in the term "Oxo-biodegradable." Oxo-degradable is generally deficient due to the existence of microplastics after the initial stage of degradation. Oxo-biodegradable formulations are designed to catalyze and accelerate the biodegradation process, ultimately leading to the incorporation of the carbon bioproducts into living microbial communities. Degradation is initially prevented by the presence of polymer stabilizers and antioxidants in the plastic. The chemical mechanism is autoxidation, but may be greatly accelerated by the presence of metal-catalysts that promote the homolysis of molecules into free radicals that drive the degradation process. Access to oxygen is essential to oxo-biodegradation, and Oxo-biodegradable plastics will not degrade if buried in a landfill or stored under other anaerobic conditions.

The inability of oxo-biodegradable plastics to degrade in landfills is a problem because landfills represent by far the largest venue in which municipal solid waste ends up. Landfills have evolved greatly in the past few decades as a result of attempts to manage methane generation. Today's landfills seek to maximize the biodegradation of materials in order to optimize methane generation rate and use. The movement is away from traditional "dry-tomb" landfills to a more biologically active landfill that is largely based upon the recirculation of leachate. When water percolates through waste, it promotes and assists the process of decomposition by bacteria and fungi. These processes in turn release by-products of decomposition and rapidly use up any available oxygen, creating an anoxic environment. In actively decomposing waste, the temperature rises and the pH falls rapidly with the result that many metal ions that are relatively insoluble at neutral pH become dissolved in the developing leachate. Leachate recirculation is the basis of today's bioreactor landfills. Additionally, as states increasingly prioritize organics waste diversion and methane emissions reduction, more anaerobic digestion plants (AD), both high-solids (dry) and low-solids (wet), are being utilized and will have a significant role in managing the spectrum of waste streams into the future. There is a clearly a pressing need for plastics that may degrade under anaerobic conditions.

The degradation of polymers under aerobic composting conditions proceeds via a sequential mechanism wherein the first step involves a simple chemical hydrolysis to reduce the molecular weight of the polymer, followed by assimilation by microorganisms which utilize the resultant oligomers as an energy source. The end result of the process is compost and near quantitative release of CO2 back into the atmosphere. The aerobic degradation is known to be highly temperature dependent, with essentially complete biodegradation in thermophilic temperatures and little degradation at mesophilic temperatures. This is consistent with the proposed two step mechanism wherein chemical hydrolysis is a prerequisite to assimilation and biodegradation. Chemical hydrolysis of is a complex phenomenon and some of the many factors which are involved include water content, temperature, crystallinity, pH, and other factors such as blended component polymers, hydrolysis stabilizer packages, end group composition, and physical form of the source polymer must be considered.

Anaerobic degradation is a biological process that transforms organic matter in an oxygen-free environment. It can follow two routes: anaerobic fermentation, where organic matter can act as an electron donor or receptor; or anaerobic respiration, which requires acceptors such as CO2, SO42−, NO3−. The process is developed in four stages: hydrolysis, acidogenesis, acetogenesis, and methanogenesis, which lead to the production of a mixture of CH4 and CO2, known as biogas. Two thirds of CH4 produced in an anaerobic process is because of the fermentation and one third by respiration. The efficiency of anaerobic biodegradation is affected by the presence of volatile fatty acids, sulfate, ammonia, and heavy metals, and for factors such as pH, temperature, redox potential, and hydrogen concentration and the type of microorganisms present in the media, presence of nutrients and the characteristics of the substrate. The degradation of plastics is usually a concurrent phenomenon involving the interaction of physical, chemical, and biological factors. The resulting mechanism will depend on the nature of the material and the environmental conditions. The factors that produce different degradation processes include UV radiation, temperature, mechanical stress, oxidative, hydrolysis, and biodegradation processes. Oxidation by oxygen and ozone will not be relevant in the case of anaerobic degradation of plastics, and the effect of photo-oxidation will be limited, as anaerobic systems are commonly carried on in closed vessels or confined spaces.

Anaerobic conditions are important for a number of end-of-life scenarios, including deep sea marine disposal, high throughput anaerobic digestion systems designed for power recovery, and landfill. Each of these will have distinctly different characteristics in terms of solids loading, microbial populations, temperature, and exposure time. The engineered high throughput anaerobic digestion systems are typically operated in the mesophilic (approx. 35-40 degrees Celsius) or thermophilic (approximately 52-60 degrees Celsius) regime. Marine disposal would be characterized by low temperatures, depending on the water depth. Landfills have been reported to have temperatures dependent on local conditions, with lower temperatures in the older waste. Moisture content also varies considerably. Some landfills are now being actively managed to act as "bioreactors", to intentionally cause microbial degradation of the waste with collection and utilization of the by-product gas.

Standards for measuring and testing oxo-biodegradable plastics include ASTM International D6954-04 "Standard Guide for Plastics that Degrade in the Environment by a Combination of Oxidation and Biodegradation." This and other relevant standards require short timescales and rapid carbon dioxide emissions. The tests performed according to ASTM D6954-04 and other comparable standards inform industry and consumers whether the plastic is degradable, biodegradable and non eco-toxic.

Completely different Standards, however, exist to characterize and test plastics degradation in an anaerobic environment. ISO 15985: "Evaluation of the ultimate anaerobic biodegradability and disintegration under high solids anaerobic digestion conditions and Method by analysis of released biogas," ASTM method D.5511-02: "Standard Test Method for Determining Anaerobic Biodegradation of Plastic Materials Under High-Solids Anaerobic Digestion Conditions," and ASTM D.5526-94 (2002): "Determining Anaerobic Biodegradation of Plastic Materials under Accelerated Landfill Conditions" help to determine the biodegradability of a material in the anaerobic and biologically active landfill environment. Rapid degradation of the plastic has the ability to increase the economic feasibility of landfill-gas recovery, minimize the duration of after-care of the landfill; and make possible the recovery of the volume reduction of the waste due to biodegradation during the active life of the landfill.

Accordingly, the flexible bag assembly 100 may include a bio-assimilator to facilitate anaerobic biodegradation. The anaerobic degradation of the flexible bag assembly 100 may meet or exceed the standards described in ASTM D.5511-02, ASTM D.5526-94 and ISO 15985 and ISO 14853. The bio-assimilator may be made from bio-sourced or artificial materials and may be included in standard or customized masterbatch formulations incorporated in the finished film production process. The bio-assimilator may include manganese stearate in its formulation as a transition metal that serves as a catalyst to trigger the free-radical process within a polyolefin material. Manganese stearate, or a similar catalyst, may be added at up to 4% to masterbatches of the Bio-assimilation additive, which may then be incorporated into polyolefin masterbatches at levels up to 1%. Alternatively, Manganese stearate may be added at up to 10% to masterbatches of the Bio-assimilation additive, which may then be incorporated into polyolefin masterbatches at levels between 0.01-3.0%.

As shown in FIGS. 9-18, the bio-assimilative additive may be used in the manufacture of other common consumer products for infants, children, caregivers and adults. For example, pacifiers 300, cups 400, containers and/or straws 500, utensils 600, bowls 700, snack catchers 800, training bibs 900, brushes 1000, sponges 1100, and bath toys 1300, are all types of consumer goods that may incorporate a bio-assimilator in order to facilitate the biodegradation of the product after its useful lifecycle. The bio-assimilative additive used in the manufacture of these products may enable the product to biodegrade anaerobically in a landfill, anaerobic digester, composter and the like according to this subject disclosure. The bio-assimilative compound may also facilitate aerobic biodegradation as well. The packaging of these items and other consumer goods may also incorporate a bio-assimilative compound to facilitate the biodegradation of the packaging in an anaerobic environment.

A bio-assimilator may be added to any of the consumer goods shown in FIGS. 9-18 with a simple inclusion rate between 0.01-2% concentration (w/w) in the masterbatch or at any time during the production process. Additionally, a bio-assimilator may comprise between 0.01-10% concentration of the plastic formulation used to manufacture the item. The consumer goods may be manufactured to contain approximately 1% of the final weight of the finished product. These products may be adapted to degrade between 1 and 60 months. These products may be adapted to degrade between 18-24 months. Alternatively, the flexible bag assembly may be adapted to degrade in approximately 36 months. Packaging may be adapted to degrade on an even faster timescale depending on its intended use in the market.

An antimicrobial such as Molybsan™, Liquid Guard™, GermGuard™, Supra-Guard™, or the like having a comparable chemical composition, may be included in the flexible bag assemblies 100 as an additive or as a coating on one or more of the layers 99a-g. Additional additives incorporated into the flexible bag assemblies 100 may include stabilizers, antistatic agents, flame retardants, plasticizers, lubricants, antiblock and slip agents, curing agents, foaming agents, catalyst deactivators, nucleators, biocides, pigments, soluble azocolorants, fillers, fiber reinforcements, and the like according to this subject disclosure. Additives in the flexible bag assemblies may be organic, inorganic or a combination of both types of compounds.

The additives used in the flexible bag assemblies 100 may be optimized for the transmission of UV light. For example, non-migratory slips reduce film clarity more than primary or secondary amides and may be avoided. The refractive index of the additive particles is also important, as differences between the additive particles and the surrounding polyolefin determine the additives' impact on clarity or haze. Haze is lower as the refractive index of the additive approaches that of the polymer. The refractive index of polyethylene is 1.5 and additives may be chosen that most closely match the refractive index of the layer 99a-g in which the additive is used. Additionally, the number of additive particles and the particle size distribution of the additive may be optimized to maximize the transmission of UV light through the flexible bag assembly 100.

Figure 2:
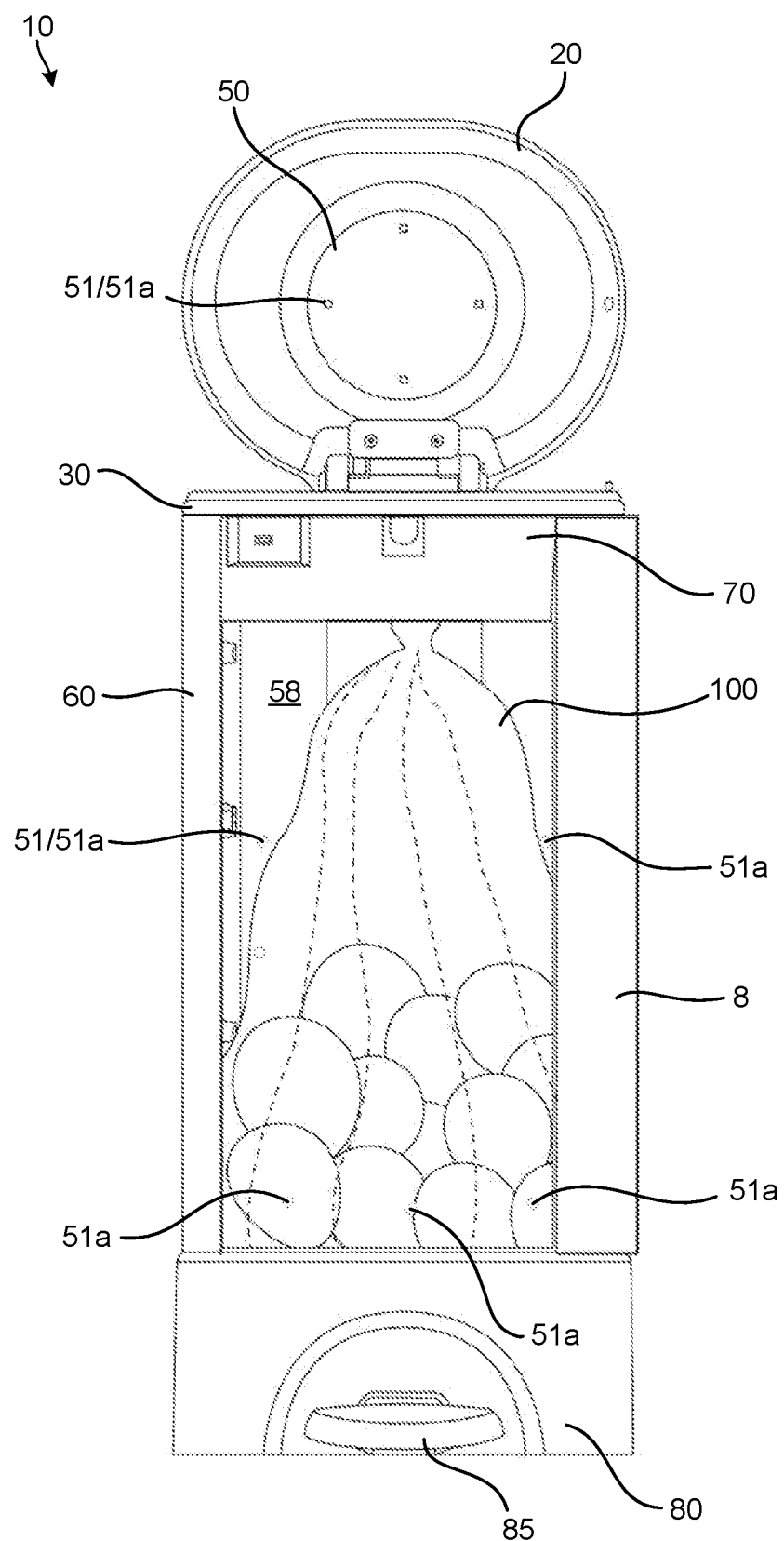
FIG. 2 is a front view of a UV sterilizing pail with a lid cover and a housing door shown in an open position with a flexible bag installed therein, according to an exemplary embodiment of the present subject disclosure.

FIG. 2 is a front view of the UV sterilizing pail 10 with a lid cover 20 of a lid assembly 40 and a door 8 of a housing 60 shown in an open position and a flexible bag assembly 100 installed in a support structure 70. The lid cover 20 may have a UV sterilizing module 50 having at least one UV light source 51 installed therein. The UV sterilizing pail 10 may include a base 80 and a foot pedal 85 and the lid assembly 40 may include an internal lid 30 and a hinge 44. The flexible bag assembly 100 and contents of its bag are shown as partially see-through in order to show UV LED lights 51a disposed in an internal storage compartment 58 of the housing 60 behind the bag assembly 100. An exemplary UV sterilizing pail 10 is described further in U.S. patent application Ser. No. 17/198,072, which is incorporated by reference herein in its entirety into this disclosure.

Figure 3:
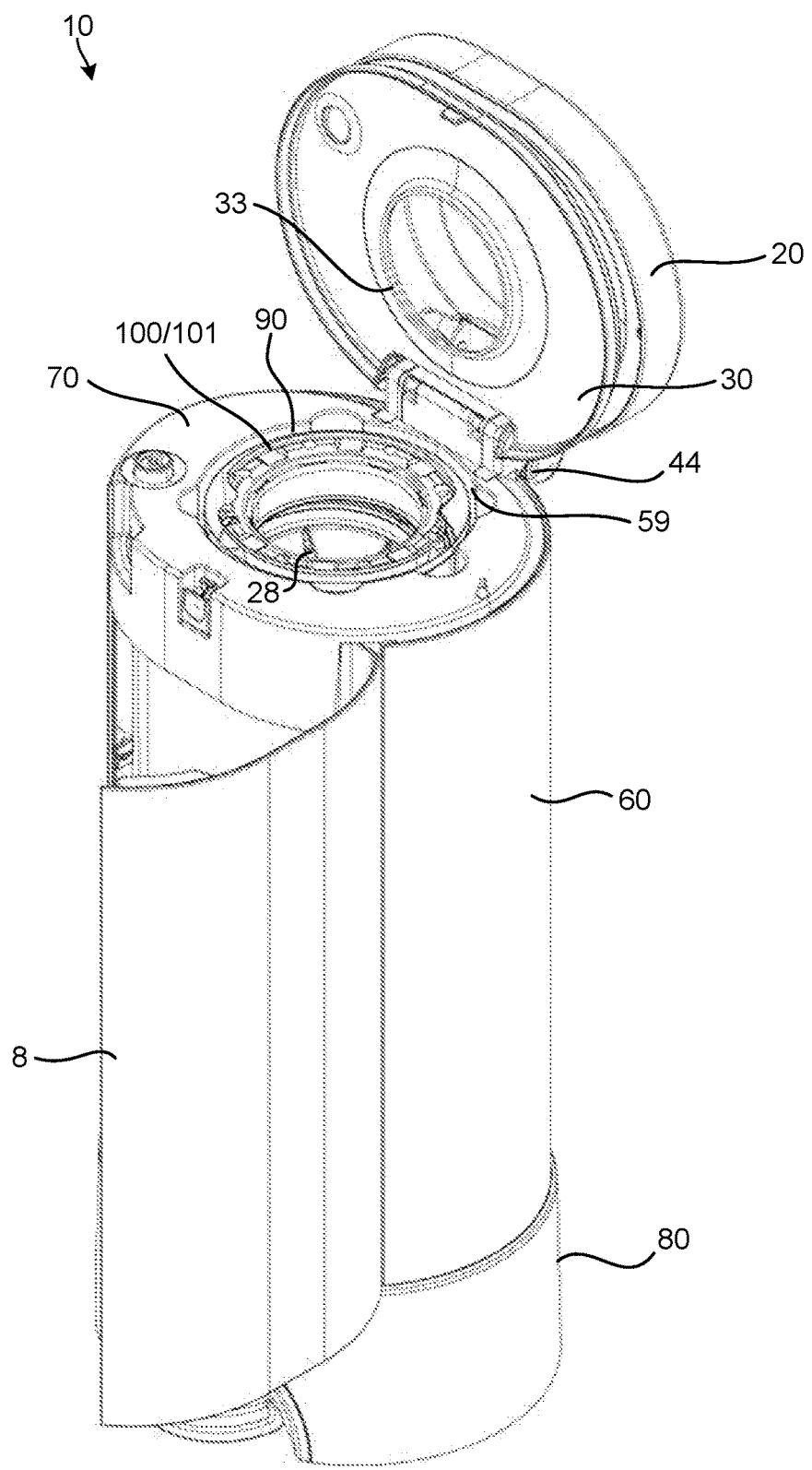
FIG. 3 is a front perspective view of a UV sterilizing pail with a lid cover and an internal lid shown in an open position with a cassette installed in a support structure, according to an exemplary embodiment of the present subject disclosure.
Figure 4:
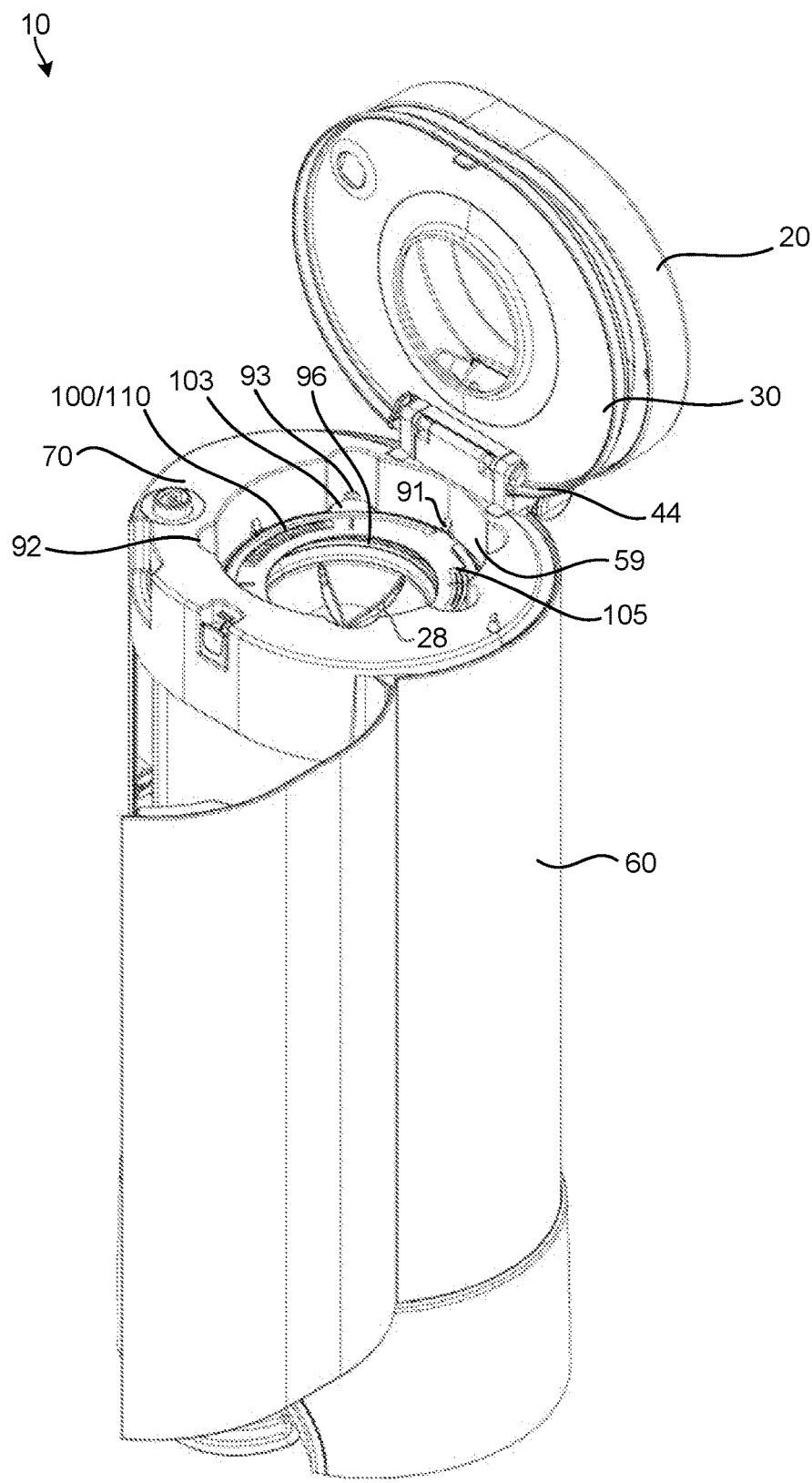
FIG. 4 is a front perspective view of a UV sterilizing pail with a lid cover and an internal lid shown in an open position with a single use flexible bag installed in a support structure, according to an exemplary embodiment of the present subject disclosure.

FIGS. 3-4 show front perspective views of the UV sterilizing pail 10 with the cover lid 20, the door 8 and an internal lid 30 shown in an open position. A waste chamber 59 is disposed in a support structure 70 of the housing 60. The waste chamber 59 is adapted to receive and secure flexible bag assemblies 100, such as cassettes 101 for dispensing pleated tubing, and single use flexible bags 110. An internal lid 30 opens and closes over the waste chamber 59 and helps to secure and captivate the flexible bag assemblies 100 in place. When the internal lid 30 is closed over the cassette 101, a slight compressive force is provided by the internal lid 30 to prevent flexible tubing 106 (FIG. 2) of the cassette 101 from being drawn outward from within the cassette 101 when waste is inserted into the UV sterilizing pail 10. Instead, when waste is inserted through an opening 28 in the UV sterilizing pail 10, the internal lid 30 controls the direction in which the flexible tubing 106 is extended, such that the flexible tubing 106 feeds into the opening 28 disposed in the waste chamber 59 that leads into an interior storage space 58. Further, when the internal lid 30 is closed, an internal downward projection on the internal lid 30 serves to press down and essentially lock the cassette 101 in position to a degree such that a corresponding interior upper portion of the cassette 101 receives the downward compression force of the downward projection lip 33. This secures the cassette 101 in place and presses down on the flexible tubing 106 with enough force as to prevent the downward movement of the flexible tubing 106 each time further waste is disposed within the UV sterilizing pail 10. Upon release of the internal lid 30, the flexible tubing 106 may be pulled out and cut by bag cutter to tie and dispose of the used flexible tubing 106, as needed. The flexible tubing 106 is then pulled down further to tie a knot and start a subsequent bag.

Figure 12:
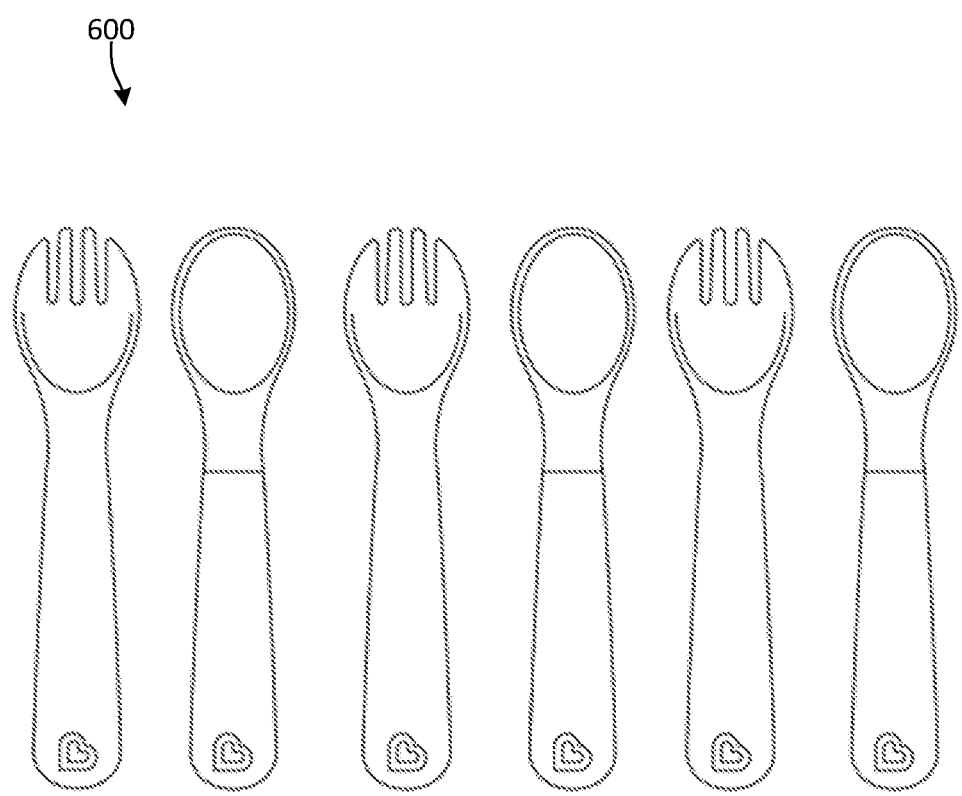
FIG. 12 is a front perspective view of multiple utensils, according to an exemplary embodiment of the present subject disclosure.
Figure 13:
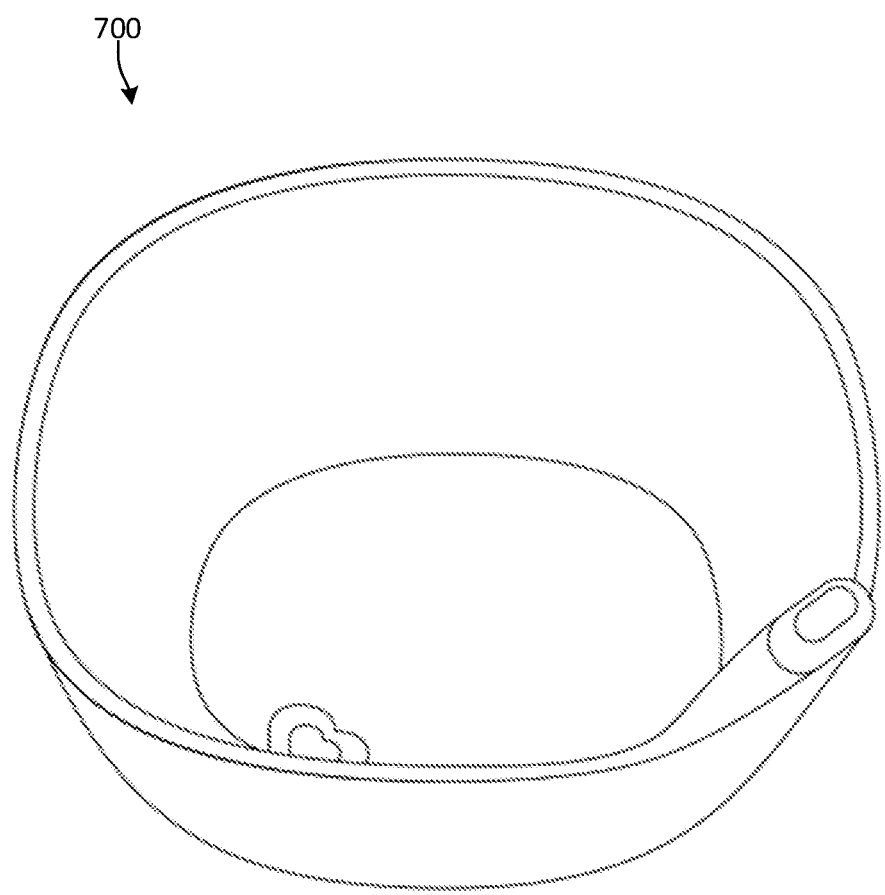
FIG. 13 is a front perspective view of a bowl, according to an exemplary embodiment of the present subject disclosure.
Figure 14:
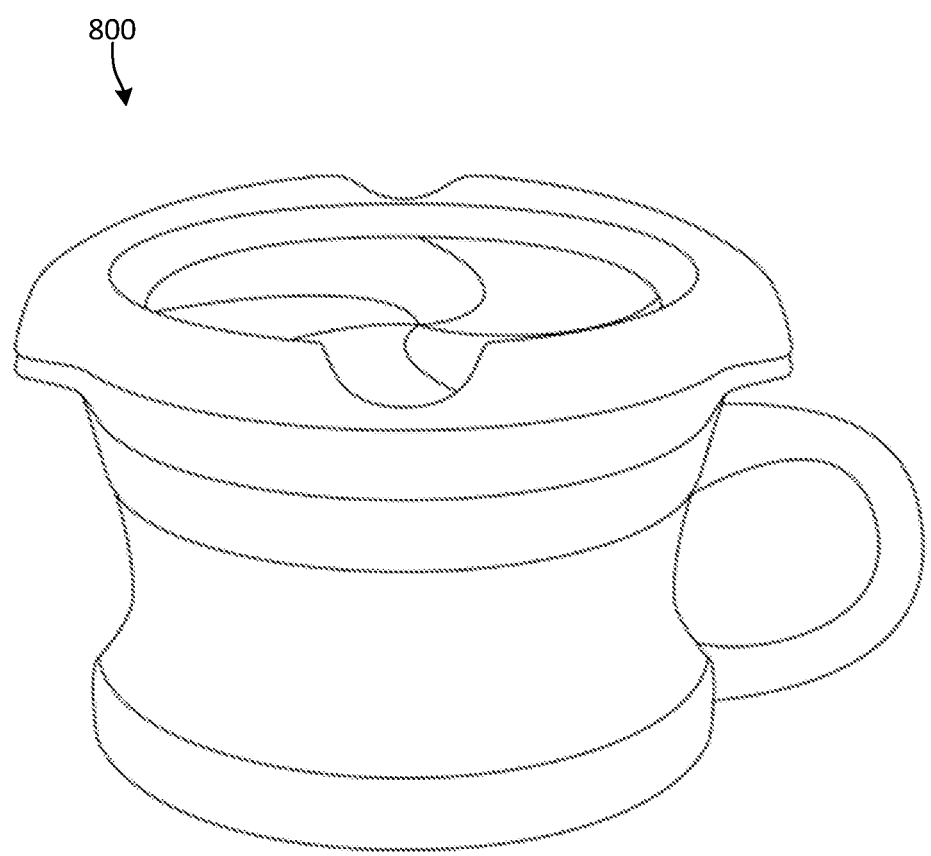
FIG. 14 is a front perspective view of a container, according to an exemplary embodiment of the present subject disclosure.
Figure 15:
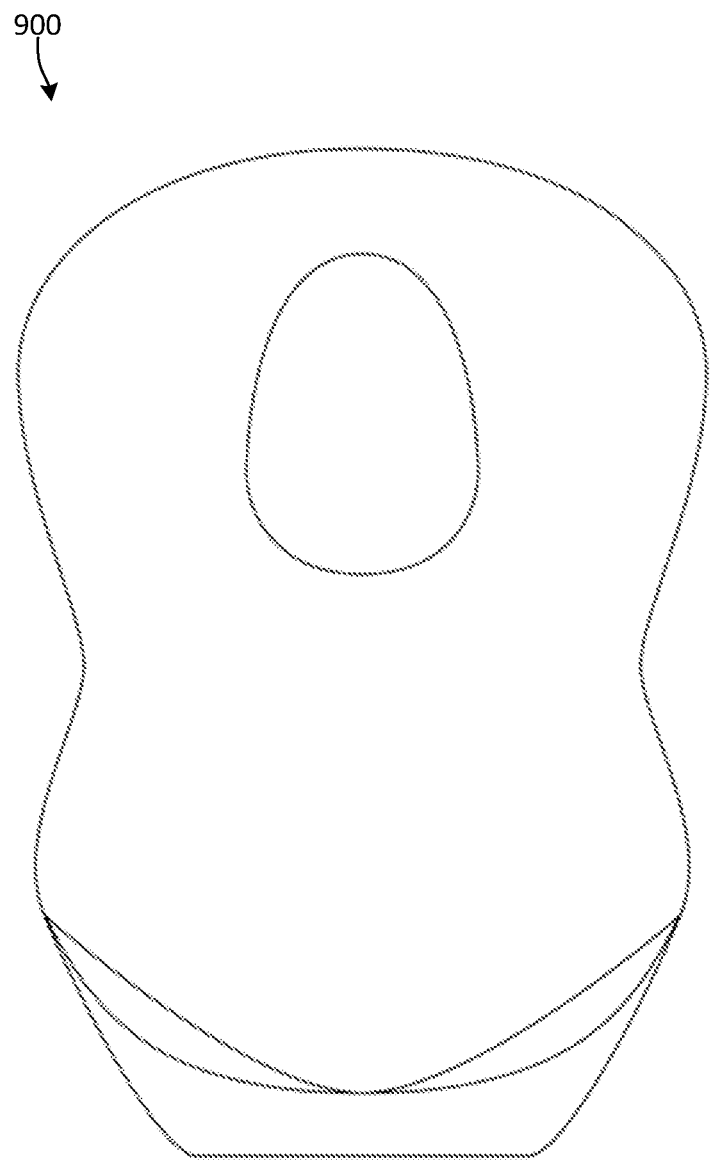
FIG. 15 is a front perspective view of a bib, according to an exemplary embodiment of the present subject disclosure.
Figure 16:
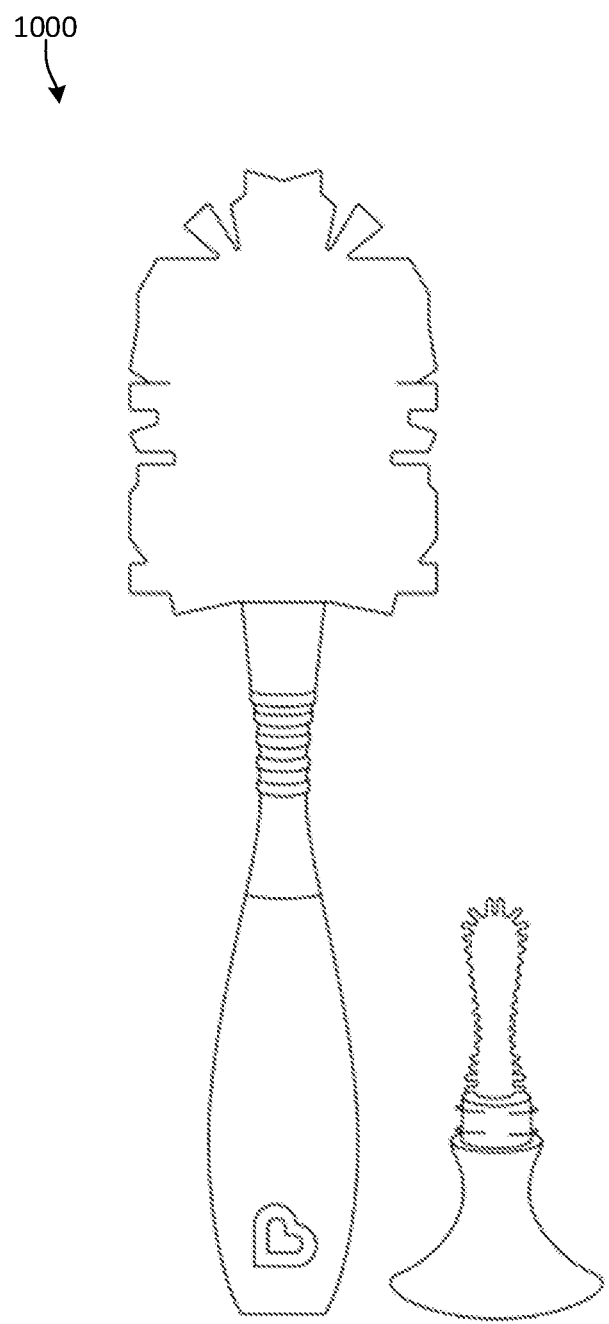
FIG. 16 is a front perspective view of a bottle brush with a detachable nipple brush, according to an exemplary embodiment of the present subject disclosure.
Figure 17:
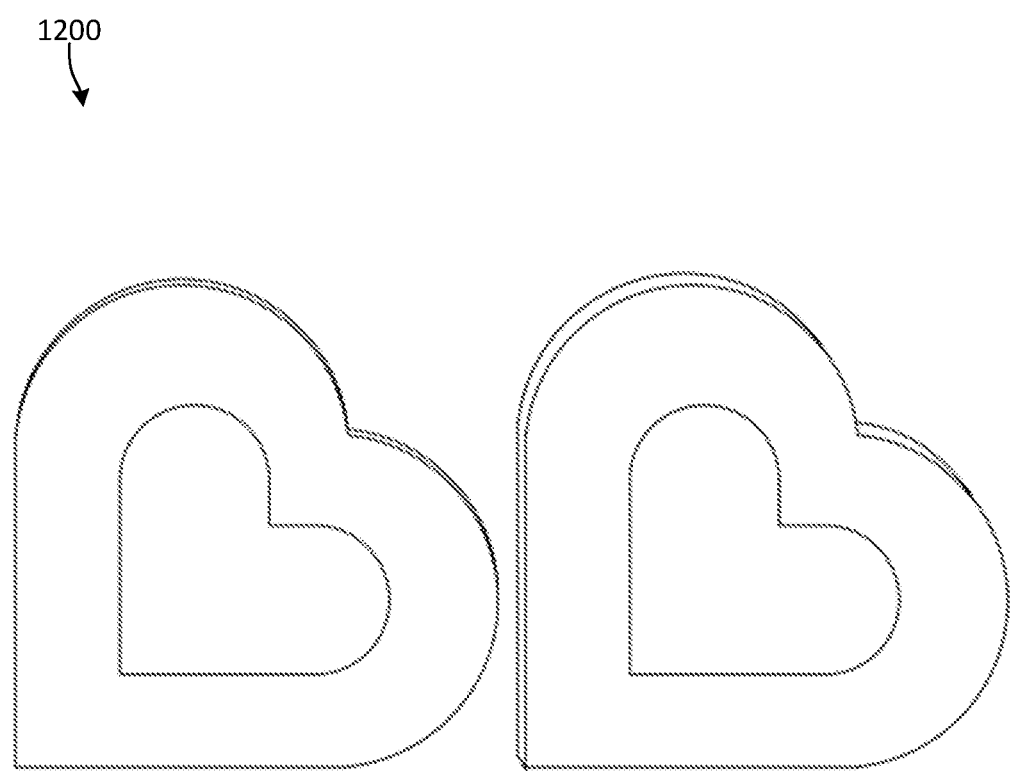
FIG. 17 is a front perspective view of two sponges, according to an exemplary embodiment of the present subject disclosure.
Figure 18:
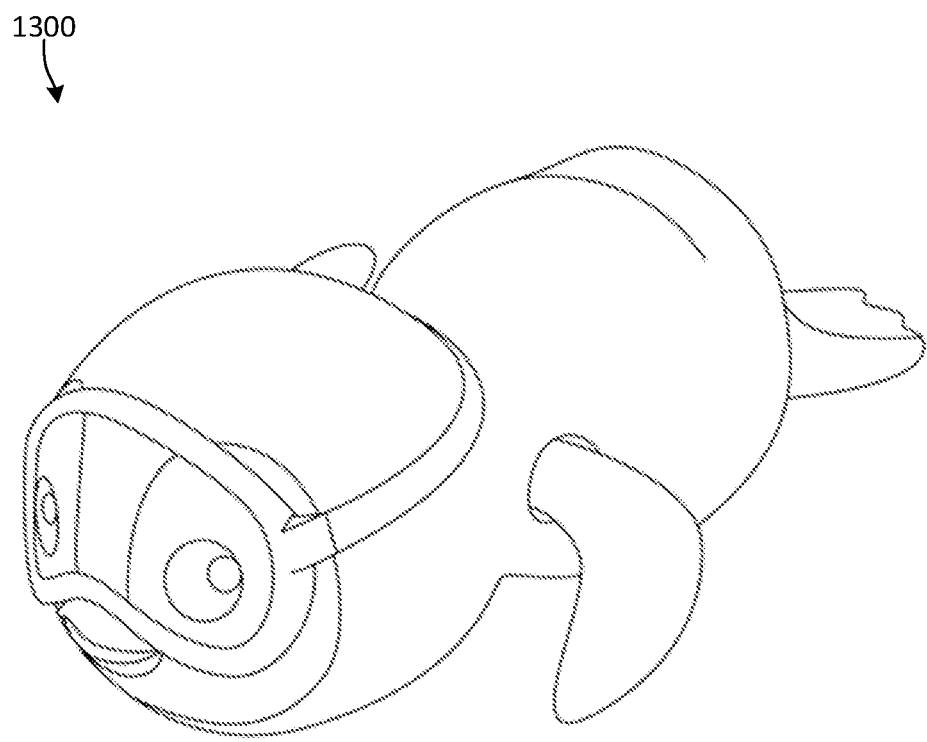
FIG. 18 is a front perspective view of a bath toy, according to an exemplary embodiment of the present subject disclosure.

In FIG. 3, the cassette 101 for dispensing pleated tubing is installed in the waste chamber 59 of the UV sterilizing pail 10. In FIG. 12, the single use flexible bag 110 having a frame 105 is installed in the waste chamber 59.

Figure 5:
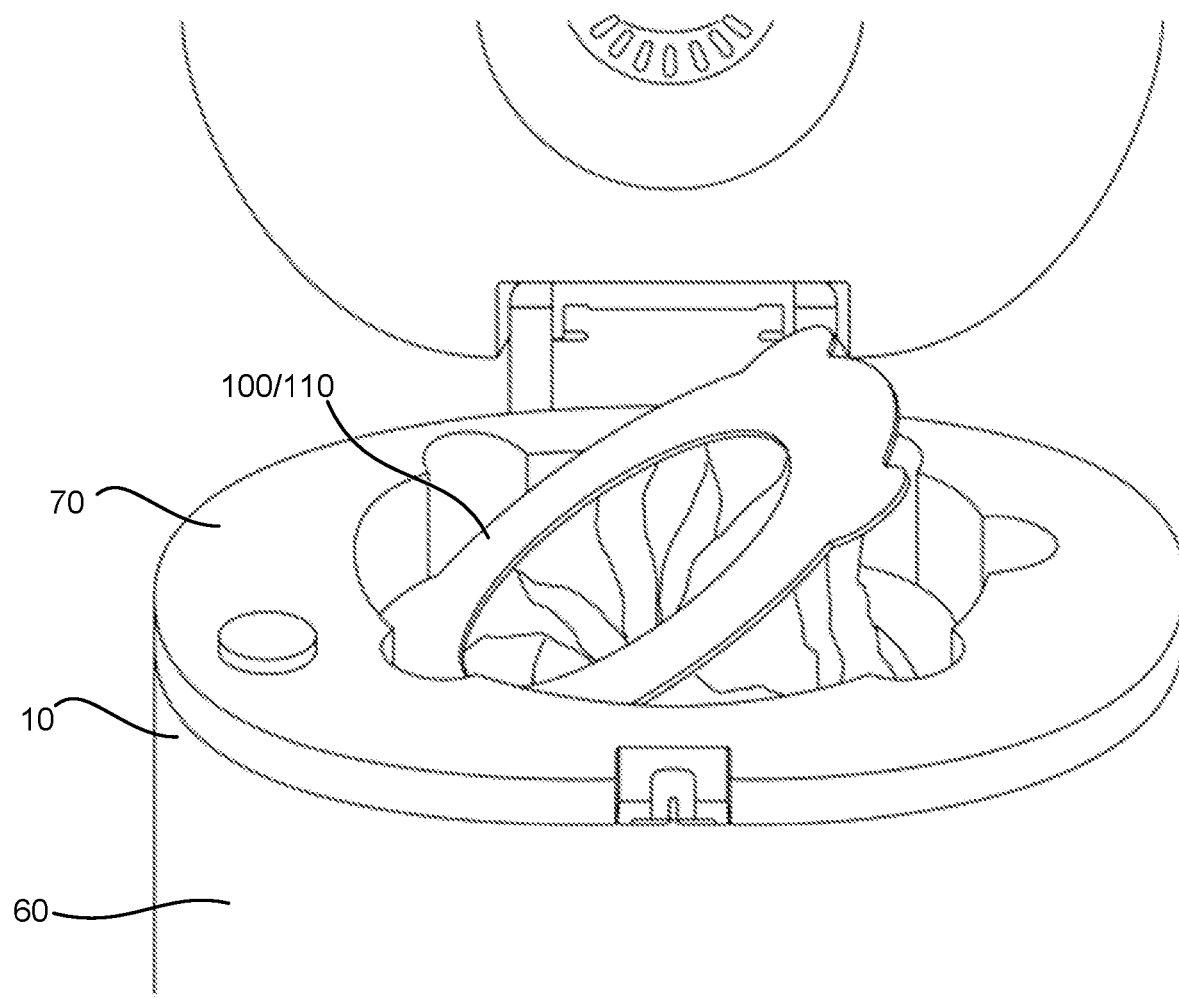
FIG. 5 is a close-up front perspective view of the UV sterilizing pail with a single use flexible bag installed therein, according to an exemplary embodiment of the present subject disclosure.
Figure 6:
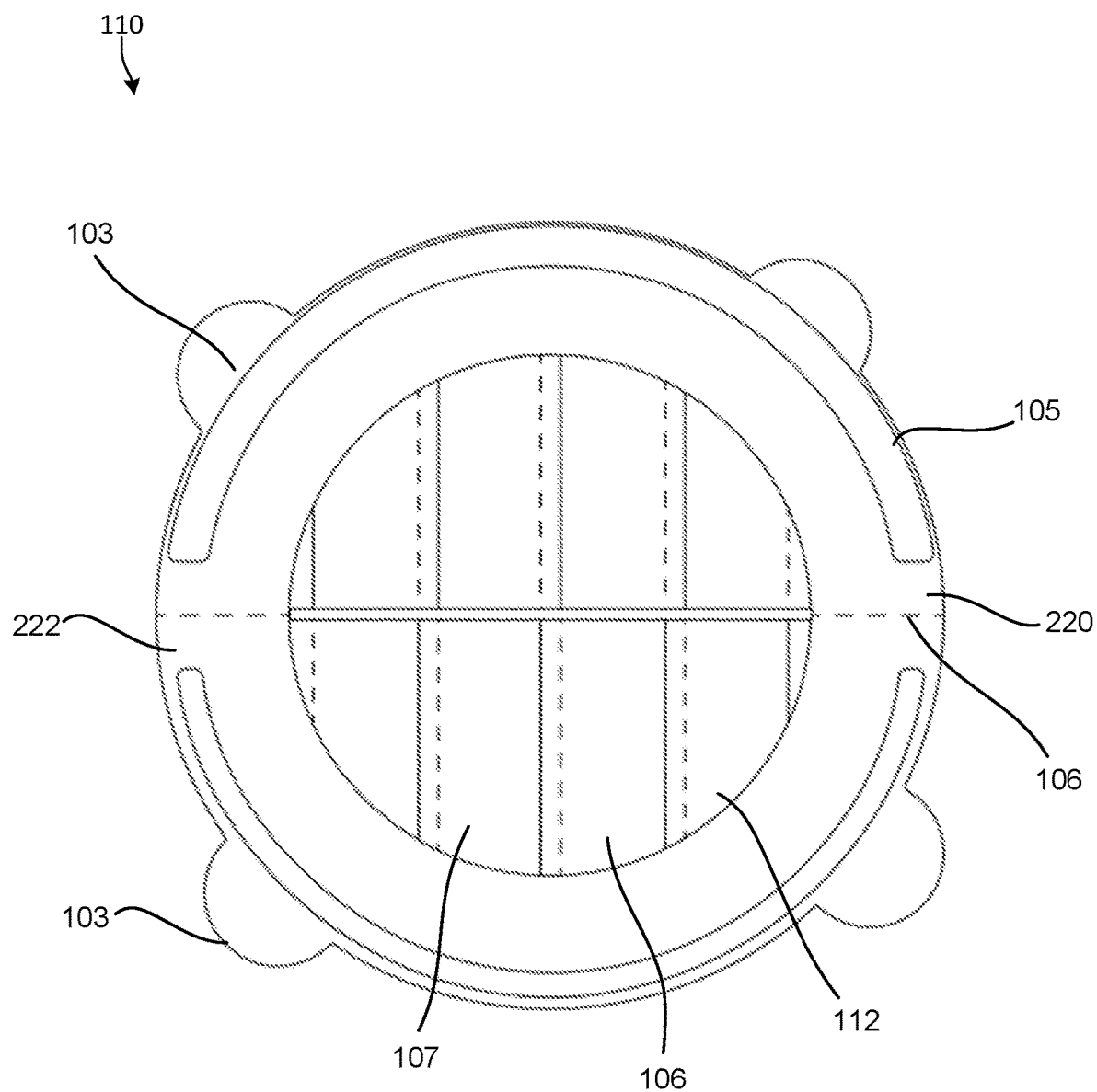
FIG. 6 is a top view of a single use flexible bag, according to an exemplary embodiment of the present subject disclosure.

An exemplary embodiment of the single use flexible bag 110 is shown in FIGS. 5-6. FIG. 5 is a front perspective view of the single use flexible bag 110 installed in a diaper pail 10. FIG. 6 is a top view of the flexible bag assembly 110 that includes flexible tubing 106 forming a bag 112 and a bag frame 105 preferably fabricated from a plastic material such as high density polyethylene. The frame 105 includes a first portion 220 that is generally semicircular in shape and a second portion 222 that is also generally semicircular in shape that encircle a central opening 107. The bag frame 105 is preferably constructed so as to be foldable about a hinge portion 106 in order to close the frame 105 around the bag 112 to prevents odors from escaping from the flexible bag 112. In addition, the bag frame 105 when in the closed position forms a convenient handle that is shaped and sized for a consumer to conveniently grip in order to carry the flexible bag 112 for final disposal.

Figure 7:
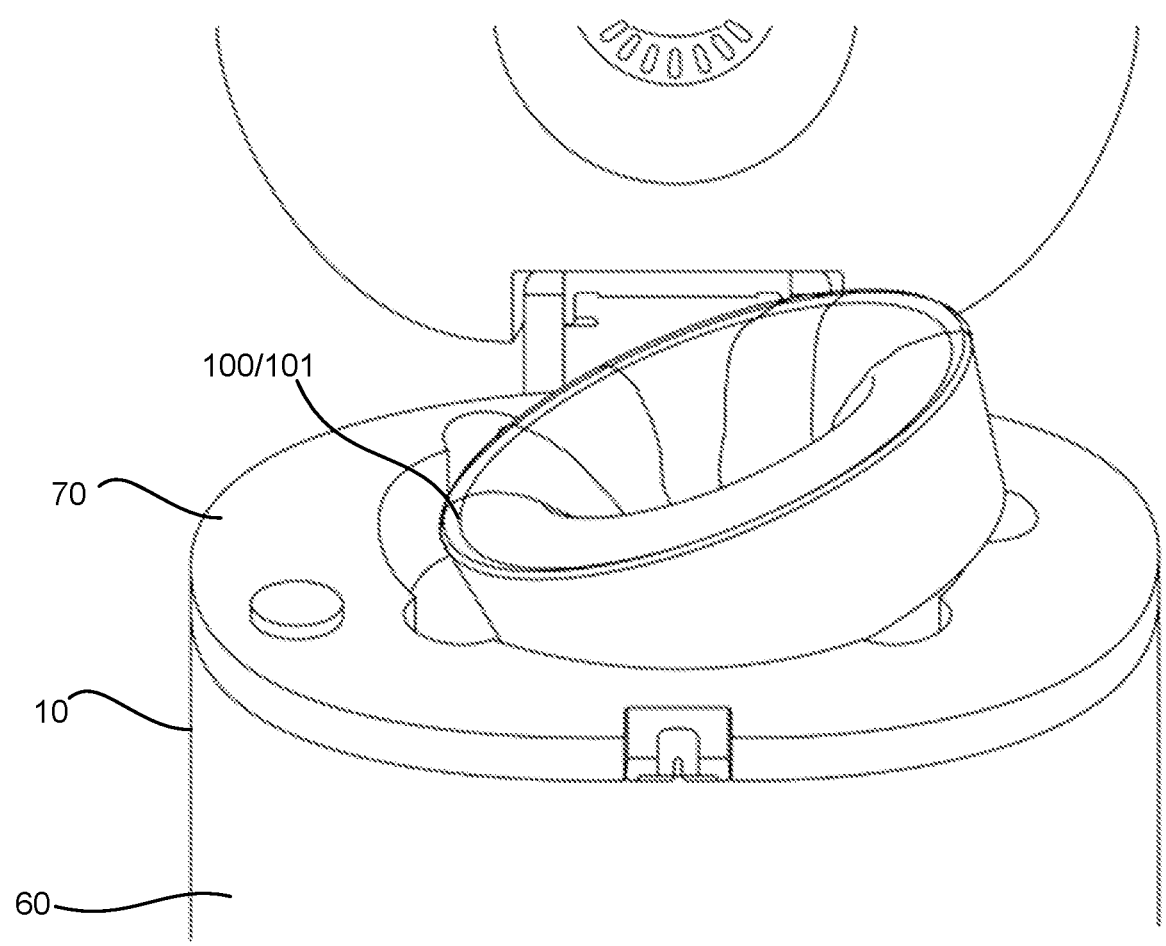
FIG. 7 is a close-up front perspective view of the UV sterilizing pail with a cassette installed therein, according to an exemplary embodiment of the present subject disclosure.
Figure 8:
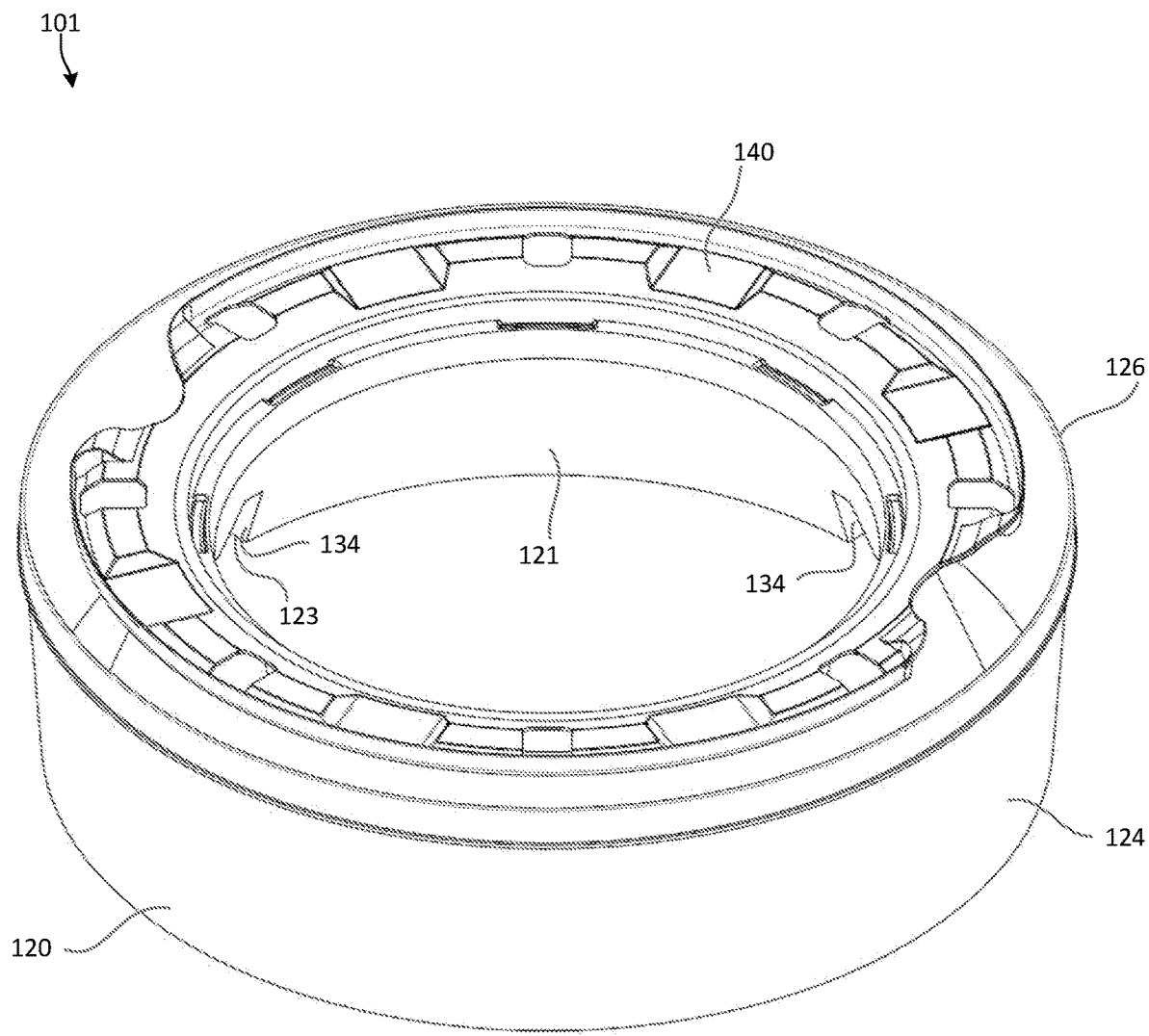
FIG. 8 is a front perspective view of a cassette for dispensing flexible tubing, according to an exemplary embodiment of the present subject disclosure.
Figure 9:
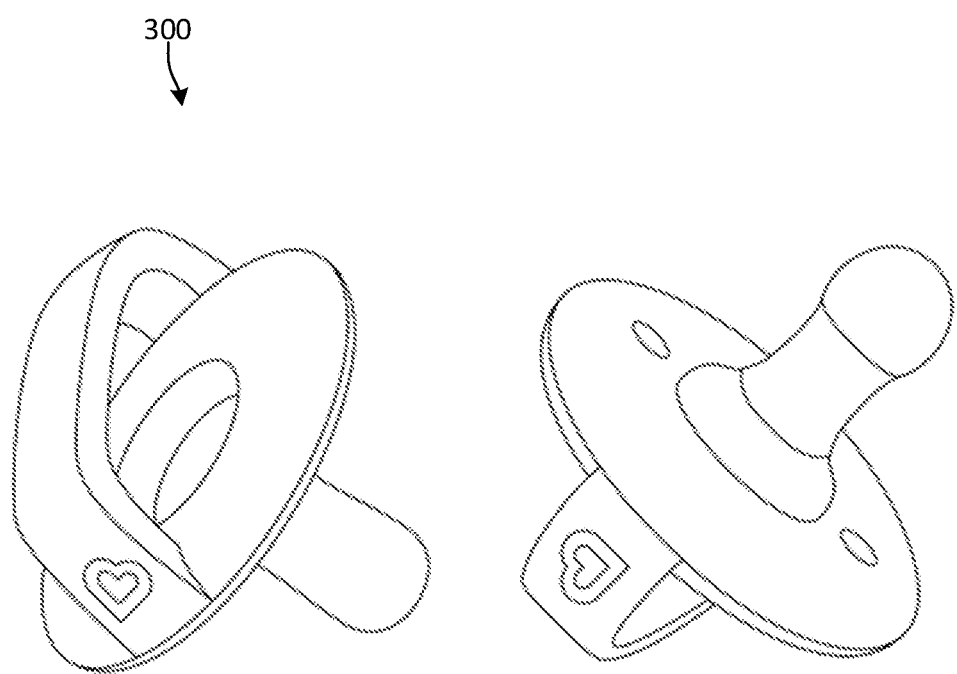
FIG. 9 is a front perspective view of two pacifiers, according to an exemplary embodiment of the present subject disclosure.
Figure 10:
FIG. 10 is a front perspective view of toddler training cup, according to an exemplary embodiment of the present subject disclosure.
Figure 11:
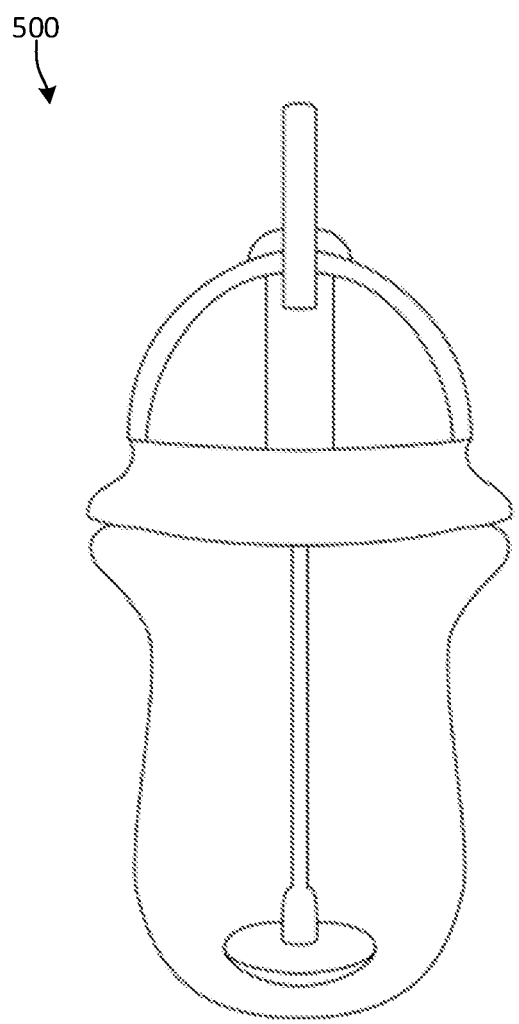
FIG. 11 is a front perspective view of a cup with a straw, according to an exemplary embodiment of the present subject disclosure.

An exemplary embodiment of a cassettes for dispensing pleated tubing 101 is shown in FIGS. 7-8. FIG. 7 is a front perspective view of the cassette 101 installed in a diaper pail 10. As shown in FIG. 8, the cassette 101 is fitted with an annular cover 140 that attaches to a lower annular body 120. The lower annular body 120 has a lower closed channel cross-section compartment comprising an inner wall 121 connected to a bottom wall 123, which is connected to an outer wall 124. The outer wall 124 terminates at an upper end 126 thereof. The inner wall 121, bottom wall 123 and outer wall 124 collectively form the lower closed channel cross-section of a housing into which pleated flexible tubing 106 is received. Two of a plurality of apertures 34 are shown disposed in the bottom of the lower annular body 20. In tilted perspective view FIG. 8, the apertures 34 are shown from an outer surface view of the inner wall 21.

As shown in FIGS. 3-4, the UV sterilizing pail 10 may be adapted for use with various styles of flexible bag assemblies 100 and may include a cylindrical recess 94 and a circular bottom receiving plate 96 having a first support structure or support member 90 and a second support structure or support member 91 for accommodating the flexible bag assemblies 100. The first support structure 90 may be adapted to hold and secure the single use flexible bag 110. The first support structure 90 may include recesses 92 having a semi-circular shape for receiving external tabs 103 of the frame 105 of the single use flexible bag 110 and securing these tabs 103 in place by use of a tab clip 93. The second support structure 91 may be adapted to hold and secure the cassette 101 and may include key projections that project upward a predetermined distance so that they mate with complementary apertures at a bottom portion of the cassette 101. The key projections may be adapted to control the position or the rotation of the cassette 101. Exemplary flexible bag support structures are described in U.S. Pat. No. 10,906,737, which is incorporated by reference herein in its entirety into this disclosure.

The UV sterilizing pail 10 may generate UV light by the UV light sources 51 to shine onto, and into, the flexible bag assembly 100 installed therein. This sterilizes both the outer and inner surfaces of the flexible bag assembly 100, but also the contents stored inside of the flexible bag assembly 100. The flexible bag assembly 100 may be adapted to transmit UV light, and UV-C light specifically, in order to maximize the penetration of the UV light generated by the UV light sources 51 disposed in the UV sterilizing pail 10. These optimized flexible bag assemblies 100 may increase the penetration and effectiveness of the UV-C light well beyond the normal UV-C transmissive properties of current bags known in the art.

The optical properties of PE-based films vary between clear (transparent), partially opaque (translucent) or opaque depending on the thermal history and film thickness of the material. LDPE has the greatest transparency, LLDPE slightly less, while high density polyethylene (HDPE) has the least transparency. Transparency is reduced by crystallites if they are larger than the wavelength of the transmitted light. The flexible bag assemblies 100 may be transparent or translucent and adapted to maximize the transmission of UV light. The flexible bag assemblies 100 may be manufactured to minimize the presence of scattering centers in the material.

The addition of additives, such as pigments, in the manufacturing of PE films introduce color centers that absorb light or scattering centers that interrupt the light traveling through the film. Ideally, the PE materials used in the construction of the flexible bag assemblies 100 will be as free of such additives as possible. Construction of the flexible bag assemblies 100 may balance the physical use-constraints of the flexible bag assemblies 100 with those properties that maximize optical transparency and the transmission of high energy, high frequency, small wavelength UV light.

The surface of the flexible bag assemblies 100 may be non-ionic and inert to minimize reactivity and denaturation. The composition of the flexible bag assemblies 100 may be polarized to only allows certain desirable wavelengths through the flexible bag assemblies 100. The flexible bag assemblies 100 may have an optimized geometry for the transmission of UV light. The flexible bag assemblies may have an optimized chemical formulation and molecular structure to maximize the transmission of UV light. The layers 99a-g of the flexible bag assemblies may have a coordinated geometry between the various layers 99a-g in order to introduce UV transmission pathways through the layers 99a-g exhibiting a high level of optical transparency. The surface layers 99a, 99g may have an optimized geometry to promote the transmission of UV light. The surface layers may exhibit natural patterns, symmetry, periodic tiling, spirals, waves, foam structure and the like according to this subject disclosure. Depending on the process used in the manufacturing process, this optimized geometry, such as periodic windows or channels of high optical transparency and clarity, may be repeated throughout the length and width of the flexible bag assemblies 100.

The illustrations and examples provided herein are for explanatory purposes and are not intended to limit the scope of the appended claims. It will be recognized by those skilled in the art that changes or modifications may be made to the above described embodiment without departing from the broad inventive concepts of the invention. It is understood therefore that the invention is not limited to the particular embodiments described herein, but is intended to cover all modifications and changes within the scope and spirit of the invention.

What is claimed:

1. A flexible bag assembly comprising:
    at least one layer of a flexible material that permits a UV light source to penetrate through the flexible material to sterilize contents on a side opposite the UV light source, wherein a reduction rate of a transmission of the UV light source through the flexible material is low to enhance a kill rate of bacterial within an interior of the flexible bag assembly.

2. The flexible bag assembly recited in claim 1, further comprising:
    a bio-assimilator added to a composition of the flexible bag assembly to biodegrade plastic to a molecular weight that is consumed by living organisms by anaerobic degradation leaving no microplastic remnants.

3. The flexible bag assembly recited in claim 1, wherein the flexible bag assembly is a cassette having a flexible tubing contained within, the flexible tubing being made of the flexible material.

4. The flexible bag assembly recited in claim 1, wherein the flexible bag assembly is a single use bag with a frame, the single use bag being made of the flexible material.

5. The flexible bag assembly recited in claim 1, wherein the flexible material is constructed with more than one layer.

6. The flexible bag assembly recited in claim 1, wherein the flexible bag assembly is installed in a waste container having at least one UV light source disposed therein.

7. The flexible bag assembly recited in claim 6, wherein the waste container is a diaper pail.

8. The flexible bag assembly recited in claim 7, wherein the UV light source is more than one UV light source disposed throughout the diaper pail.

9. The flexible bag assembly recited in claim 6, wherein the UV light source is provided in a lid of the waste container.

10. The flexible bag assembly recited in claim 6, wherein the UV light source is provided on an internal wall of the waste chamber.

11. A flexible bag assembly comprising:
at least one layer of a flexible material that permits a UV light source to penetrate through the flexible material to sterilize contents on an interior of the flexible bag assembly, wherein a reduction rate of a transmission of the UV light source through the flexible material is low to enhance a kill rate of bacterial within the interior of the flexible bag assembly; and
a bio-assimilator integrated into a composition of the flexible bag assembly to biodegrade plastic to a molecular weight that is consumed by living organisms by anaerobic degradation leaving no microplastic remnants.

12. The flexible bag assembly recited in claim 11, wherein the flexible bag assembly is a cassette having a flexible tubing disposed therein, the flexible tubing made from the flexible material.

13. The flexible bag assembly recited in claim 11, wherein the flexible bag assembly is a single use bag with a frame, the single use bag made from the flexible material.

14. The flexible bag assembly recited in claim 11, wherein the flexible bag assembly is installed in a diaper pail having at least one UV light source disposed therein.

15. The flexible bag assembly recited in claim 14, wherein the UV light source is more than one UV light source disposed throughout the pail.

16. A flexible bag assembly comprising:
a multilayer flexible material that permits a UV light source to penetrate through the multilayer flexible material to sterilize contents on an interior of the flexible bag assembly, wherein a reduction rate of a transmission of the UV light source through the multilayer flexible material is low to enhance a kill rate of bacterial within the interior of the flexible bag assembly,
wherein the flexible bag assembly is installed in a waste container having at least one UV light source disposed therein.

17. The flexible bag assembly recited in claim 16, further comprising:
a bio-assimilator integrated into a composition of the multilayer flexible material to biodegrade plastic to a molecular weight that is consumed by living organisms by anaerobic degradation is leaving no microplastic remnants.

18. The flexible bag assembly recited in claim 16, further comprising:
a bio-assimilator integrated into a composition of the flexible bag assembly to biodegrade plastic to a molecular weight that is consumed by living organisms by anaerobic degradation leaving no microplastic remnants.

19. The flexible bag assembly recited in claim 18, wherein the bio-assimilator is added in the range between 0.01-10% concentration of a plastic formulation used to manufacture the flexible bag assembly.

20. The flexible bag assembly recited in claim 16, wherein the flexible bag assembly is installed in a diaper pail having multiple UV light source disposed therein.

* * * * *